(12) United States Patent
Leng

(10) Patent No.: US 6,890,745 B1
(45) Date of Patent: May 10, 2005

(54) PROTEASE SPECIFIC CLEAVABLE LUCIFERASES AND METHODS OF USE THEREOF

(75) Inventor: Jay Leng, San Diego, CA (US)

(73) Assignee: Chemicon International, Inc., Temecula, CA (US)

( * ) Notice: Subject to any disclaimer, the term of this patent is extended or adjusted under 35 U.S.C. 154(b) by 420 days.

(21) Appl. No.: 09/619,047

(22) Filed: Jul. 19, 2000

(51) Int. Cl.$^7$ .................. C12N 9/02; C12N 9/48; C12N 15/00; C07H 21/04
(52) U.S. Cl. ............. 435/189; 435/212; 435/440; 536/23.2; 536/23.1; 536/23.4
(58) Field of Search ............... 435/189, 212, 435/440, 4, 8; 536/23.2, 23.1, 23.4; 530/380

(56) References Cited

FOREIGN PATENT DOCUMENTS

WO      WO 98/14605     4/1998

OTHER PUBLICATIONS

Korant et al. Cleavage of Cellular Proteins by the HIV–1 Protease. Proteolysis in Cell Functions. (1997), 13, pp. 520–523.*
Thompson et al. The Journal of Biological Chemistry, vol. 272, No. 30, pp. 18766–18771, 1997.*
Lorenz et al. J. Biolumin Chemlumin, vol. 11, pp. 31–37, 1996.*
Xu et al. Nucleci Acids Research, vol. 26, No. 8, pp. 2034–2035, 1998.*
Korant et al., "Clevage of Cellular Proteins by the HIV–1 Protease", *Biochemical and Health Research*, 1997, pp. 520–523.
Wang et al., "The *Renilla* Luciferase–Modified GFP Fusion Protein is Functional in Transformed Cells" *Biohydrogen, 'Proceedings of an International Conference on Biological Hydrogen Production'* Waikoloa, HI, Jun. 23–26, 1997.
Liu et al., "Visualizing and Quantifying Protein Secretion Using a *Renilla* Luciferase–GFP Fusion Protein", *Luminescence (Chichester)*, vol. 15, No. 1, Jan. 2000, pp. 45–49.
Leng et al., "CleavaLite™ : A Novel Bioluminescent Caspase Activity Assay", *Society for Neuroscience Abstracts*, vol. 27, No. 2, 2001, p. 1555.

* cited by examiner

Primary Examiner—Ponnathapu Achutamurthy
Assistant Examiner—Yong D. Pak
(74) Attorney, Agent, or Firm—Gray Cary Ware & Freidenrich, LLP

(57) ABSTRACT

Provided are methods and compositions useful in detecting protease activity in a sample, as well as methods of identifying agents that modulate protease activity. The methods and compositions provide a modified luciferase polynucleotide sequence and a luciferase polypeptide containing protease recognition sequences, wherein cleavage of the recognition sequence by a protease inhibits luciferase activity. Further provided are methods and compositions for detecting and modulating caspase activity and apoptosis.

5 Claims, 6 Drawing Sheets

SEQUENCE LISTING

<160> NUMBER OF SEQ ID NOS: 29

<210> SEQ ID NO 1
<211> LENGTH: 936
<212> TYPE: DNA
<213> ORGANISM: Renilla reniformis
<220> FEATURE:
<221> NAME/KEY: CDS
<222> LOCATION: (1)..(936)

<400> SEQUENCE: 1

| | | | | | | | | | | | | | | | | |
|---|---|---|---|---|---|---|---|---|---|---|---|---|---|---|---|---|
| atg | act | tcg | aaa | gtt | tat | gat | cca | gaa | caa | agg | aaa | cgg | atg | ata | act | 48 |
| Met | Thr | Ser | Lys | Val | Tyr | Asp | Pro | Glu | Gln | Arg | Lys | Arg | Met | Ile | Thr | |
| 1 | | | | 5 | | | | | 10 | | | | | 15 | | |
| ggt | ccg | cag | tgg | tgg | gcc | aga | tgt | aaa | caa | atg | aat | gtt | ctt | gat | tca | 96 |
| Gly | Pro | Gln | Trp | Trp | Ala | Arg | Cys | Lys | Gln | Met | Asn | Val | Leu | Asp | Ser | |
| | | | 20 | | | | | 25 | | | | | 30 | | | |
| ttt | att | aat | tat | tat | gat | tca | gaa | aaa | cat | gca | gaa | aat | gct | gtt | att | 144 |
| Phe | Ile | Asn | Tyr | Tyr | Asp | Ser | Glu | Lys | His | Ala | Glu | Asn | Ala | Val | Ile | |
| | | 35 | | | | | 40 | | | | | 45 | | | | |
| ttt | tta | cat | ggt | aac | gcg | gcc | tct | tct | tat | tta | tgg | cga | cat | gtt | gtg | 192 |
| Phe | Leu | His | Gly | Asn | Ala | Ala | Ser | Ser | Tyr | Leu | Trp | Arg | His | Val | Val | |
| | 50 | | | | | 55 | | | | | 60 | | | | | |
| cca | cat | att | gag | cca | gta | gcg | cgg | tgt | att | ata | cca | gat | ctt | att | ggt | 240 |
| Pro | His | Ile | Glu | Pro | Val | Ala | Arg | Cys | Ile | Ile | Pro | Asp | Leu | Ile | Gly | |
| 65 | | | | | 70 | | | | | 75 | | | | | 80 | |
| atg | ggc | aaa | tca | ggc | aaa | tct | ggt | aat | ggt | tct | tat | agg | tta | ctt | gat | 288 |
| Met | Gly | Lys | Ser | Gly | Lys | Ser | Gly | Asn | Gly | Ser | Tyr | Arg | Leu | Leu | Asp | |
| | | | | 85 | | | | | 90 | | | | | 95 | | |
| cat | tac | aaa | tat | ctt | act | gca | tgg | ttt | gaa | ctt | ctt | aat | tta | cca | aag | 336 |
| His | Tyr | Lys | Tyr | Leu | Thr | Ala | Trp | Phe | Glu | Leu | Leu | Asn | Leu | Pro | Lys | |
| | | | 100 | | | | | 105 | | | | | 110 | | | |
| aag | atc | att | ttt | gtc | ggc | cat | gat | tgg | ggt | gct | tgt | ttg | gca | ttt | cat | 384 |
| Lys | Ile | Ile | Phe | Val | Gly | His | Asp | Trp | Gly | Ala | Cys | Leu | Ala | Phe | His | |
| | | 115 | | | | | 120 | | | | | 125 | | | | |
| tat | agc | tat | gag | cat | caa | gat | aag | atc | aaa | gca | ata | gtt | cac | gct | gaa | 432 |
| Tyr | Ser | Tyr | Glu | His | Gln | Asp | Lys | Ile | Lys | Ala | Ile | Val | His | Ala | Glu | |
| | 130 | | | | | 135 | | | | | 140 | | | | | |
| agt | gta | gta | gat | gtg | att | gaa | tca | tgg | gat | gaa | tgg | cct | gat | att | gaa | 480 |
| Ser | Val | Val | Asp | Val | Ile | Glu | Ser | Trp | Asp | Glu | Trp | Pro | Asp | Ile | Glu | |
| 145 | | | | | 150 | | | | | 155 | | | | | 160 | |
| gaa | gat | att | gcg | ttg | atc | aaa | tct | gaa | gaa | gga | gaa | aaa | atg | gtt | ttg | 528 |
| Glu | Asp | Ile | Ala | Leu | Ile | Lys | Ser | Glu | Glu | Gly | Glu | Lys | Met | Val | Leu | |
| | | | | 165 | | | | | 170 | | | | | 175 | | |
| gag | aat | aac | ttc | ttc | gtg | gaa | acc | atg | ttg | cca | tca | aaa | atc | atg | aga | 576 |
| Glu | Asn | Asn | Phe | Phe | Val | Glu | Thr | Met | Leu | Pro | Ser | Lys | Ile | Met | Arg | |
| | | | 180 | | | | | 185 | | | | | 190 | | | |
| aag | tta | gaa | cca | gaa | gaa | ttt | gca | gca | tat | ctt | gaa | cca | ttc | aaa | gag | 624 |
| Lys | Leu | Glu | Pro | Glu | Glu | Phe | Ala | Ala | Tyr | Leu | Glu | Pro | Phe | Lys | Glu | |
| | | 195 | | | | | 200 | | | | | 205 | | | | |
| aaa | ggt | gaa | gtt | cgt | cgt | cca | aca | tta | tca | tgg | cct | cgt | gaa | atc | ccg | 672 |
| Lys | Gly | Glu | Val | Arg | Arg | Pro | Thr | Leu | Ser | Trp | Pro | Arg | Glu | Ile | Pro | |
| | 210 | | | | | 215 | | | | | 220 | | | | | |
| tta | gta | aaa | ggt | ggt | aaa | cct | gac | gtt | gta | caa | att | gtt | agg | aat | tat | 720 |
| Leu | Val | Lys | Gly | Gly | Lys | Pro | Asp | Val | Val | Gln | Ile | Val | Arg | Asn | Tyr | |
| 225 | | | | | 230 | | | | | 235 | | | | | 240 | |
| aat | gct | tat | cta | cgt | gca | agt | gat | gat | tta | cca | aaa | atg | ttt | att | gaa | 768 |
| Asn | Ala | Tyr | Leu | Arg | Ala | Ser | Asp | Asp | Leu | Pro | Lys | Met | Phe | Ile | Glu | |
| | | | | 245 | | | | | 250 | | | | | 255 | | |

-continued

```
tcg gat cca gga ttc ttt tcc aat gct att gtt gaa ggc gcc aag aag    816
Ser Asp Pro Gly Phe Phe Ser Asn Ala Ile Val Glu Gly Ala Lys Lys
        260                 265                 270 ttt cct aat act gaa ttt gtc aaa gta aaa ggt ctt cat ttt tcg caa    864
Phe Pro Asn Thr Glu Phe Val Lys Val Lys Gly Leu His Phe Ser Gln
        275                 280                 285 gaa gat gca cct gat gaa atg gga aaa tat atc aaa tcg ttc gtt gag    912
Glu Asp Ala Pro Asp Glu Met Gly Lys Tyr Ile Lys Ser Phe Val Glu
        290                 295                 300 cga gtt ctc aaa aat gaa caa taa                                    936
Arg Val Leu Lys Asn Glu Gln
305                 310
```

<210> SEQ ID NO 2
<211> LENGTH: 311
<212> TYPE: PRT
<213> ORGANISM: Renilla reniformis

<400> SEQUENCE: 2

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu

```
                  290                 295                 300
Arg Val Leu Lys Asn Glu Gln
305                 310

<210> SEQ ID NO 3
<211> LENGTH: 936
<212> TYPE: DNA
<213> ORGANISM: Renilla reniformis (mutated sequence)
<220> FEATURE:
<221> NAME/KEY: CDS
<222> LOCATION: (1)..(936)

<400> SEQUENCE: 3 atg act tcg aaa gtt tat gat cca gaa caa agg aaa cgg atg ata act      48
Met Thr Ser Lys Val Tyr Asp Pro Glu Gln Arg Lys Arg Met Ile Thr
1               5                   10                  15 ggt ccg cag tgg tgg gcc aga tgt aaa caa atg aat gtt ctt gat tca      96
Gly Pro Gln Trp Trp Ala Arg Cys Lys Gln Met Asn Val Leu Asp Ser
            20                  25                  30 ttt att aat tat tat gat tca gaa aaa cat gca gaa aat gct gtt att     144
Phe Ile Asn Tyr Tyr Asp Ser Glu Lys His Ala Glu Asn Ala Val Ile
        35                  40                  45 ttt tta cat ggt aac gcg gcc tct tct tat tta tgg cga cat gtt gtg     192
Phe Leu His Gly Asn Ala Ala Ser Ser Tyr Leu Trp Arg His Val Val
    50                  55                  60 cca cat att gag cca gta gcg cgg tgt att ata cca gat ctt att ggt     240
Pro His Ile Glu Pro Val Ala Arg Cys Ile Ile Pro Asp Leu Ile Gly
65                  70                  75                  80 atg ggc aaa tca ggc aaa tct ggt aat ggt tct tat agg tta ctt gat     288
Met Gly Lys Ser Gly Lys Ser Gly Asn Gly Ser Tyr Arg Leu Leu Asp
                85                  90                  95 cat tac aaa tat ctt act gca tgg ttt gaa ctt ctt aat tta cca aag     336
His Tyr Lys Tyr Leu Thr Ala Trp Phe Glu Leu Leu Asn Leu Pro Lys
            100                 105                 110 aag atc att ttt gtc ggc cat gat tgg ggt gct tgt ttg gca ttt cat     384
Lys Ile Ile Phe Val Gly His Asp Trp Gly Ala Cys Leu Ala Phe His
        115                 120                 125 tat agc tat gag cat caa gat aag atc aaa gca ata gtt cac gct gaa     432
Tyr Ser Tyr Glu His Gln Asp Lys Ile Lys Ala Ile Val His Ala Glu
    130                 135                 140 agt gta gta gat gtg att gaa tca tgg gat gaa tgg cct gat att gaa     480
Ser Val Val Asp Val Ile Glu Ser Trp Asp Glu Trp Pro Asp Ile Glu
145                 150                 155                 160 gaa gat att gcg ttg atc aaa tct gaa gaa gga gaa aaa atg gtt ttg     528
Glu Asp Ile Ala Leu Ile Lys Ser Glu Glu Gly Glu Lys Met Val Leu
                165                 170                 175 gag aat aac ttc ttc gtg gaa acc atg ttg cca tca aaa atc atg aga     576
Glu Asn Asn Phe Phe Val Glu Thr Met Leu Pro Ser Lys Ile Met Arg
            180                 185                 190 aag tta gaa cca gac gaa gtt gac gca tat ctt gaa cca ttc aaa gag     624
Lys Leu Glu Pro Asp Glu Val Asp Ala Tyr Leu Glu Pro Phe Lys Glu
        195                 200                 205 aaa ggt gaa gtt cgt cgt cca aca tta tca tgg cct cgt gaa atc ccg     672
Lys Gly Glu Val Arg Arg Pro Thr Leu Ser Trp Pro Arg Glu Ile Pro
    210                 215                 220 tta gta aaa ggt ggt aaa cct gac gtt gta caa att gtt agg aat tat     720
Leu Val Lys Gly Gly Lys Pro Asp Val Val Gln Ile Val Arg Asn Tyr
225                 230                 235                 240 aat gct tat cta cgt gca agt gat gat tta cca aaa atg ttt att gaa     768
Asn Ala Tyr Leu Arg Ala Ser Asp Asp Leu Pro Lys Met Phe Ile Glu
                245                 250                 255
```

```
tcg gat cca gga ttc ttt tcc aat gct att gtt gaa ggc gcc aag aag      816
Ser Asp Pro Gly Phe Phe Ser Asn Ala Ile Val Glu Gly Ala Lys Lys
        260                 265                 270 ttt cct aat act gaa ttt gtc aaa gta aaa ggt ctt cat ttt tcg caa      864
Phe Pro Asn Thr Glu Phe Val Lys Val Lys Gly Leu His Phe Ser Gln
    275                 280                 285 gaa gat gca cct gat gaa atg gga aaa tat atc aaa tcg ttc gtt gag      912
Glu Asp Ala Pro Asp Glu Met Gly Lys Tyr Ile Lys Ser Phe Val Glu
290                 295                 300 cga gtt ctc aaa aat gaa caa taa                                      936
Arg Val Leu Lys Asn Glu Gln
305                 310
```

<210> SEQ ID NO 4
<211> LENGTH: 311
<212> TYPE: PRT
<213> ORGANISM: Renilla reniformis (mutated sequence)

<400> SEQUENCE: 4

```
Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Asp Glu Val Asp Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285
```

```
Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 5
<211> LENGTH: 8
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 5

Ser Gln Asn Tyr Pro Ile Val Gln
1               5

<210> SEQ ID NO 6
<211> LENGTH: 10
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 6

Lys Ala Arg Val Leu Ala Glu Ala Met Ser
1               5                   10

<210> SEQ ID NO 7
<211> LENGTH: 10
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 7

Pro Ser Pro Arg Glu Gly Lys Arg Ser Tyr
1               5                   10

<210> SEQ ID NO 8
<211> LENGTH: 5
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 8

Tyr Val Ala Asp Gly
1               5

<210> SEQ ID NO 9
<211> LENGTH: 8
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 9

Met Phe Gly Gly Ala Lys Lys Arg
1               5

<210> SEQ ID NO 10
<211> LENGTH: 10
```

```
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 10

Gly Val Val Asn Ala Ser Ser Arg Leu Ala
1               5                   10

<210> SEQ ID NO 11
<211> LENGTH: 9
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 11

Leu Ile Ala Tyr Leu Lys Lys Ala Thr
1               5

<210> SEQ ID NO 12
<211> LENGTH: 7
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 12

Val Lys Met Asp Ala Glu Phe
1               5

<210> SEQ ID NO 13
<211> LENGTH: 17
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 13

Phe Leu Ala Glu Gly Gly Gly Val Arg Gly Pro Arg Val Val Glu Arg
1               5                   10                  15

His

<210> SEQ ID NO 14
<211> LENGTH: 13
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 14

Asp Arg Val Tyr Ile His Pro Phe His Leu Val Ile His
1               5                   10

<210> SEQ ID NO 15
<211> LENGTH: 8
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 15
```

```
Lys Pro Ala Leu Phe Phe Arg Leu
1               5

<210> SEQ ID NO 16
<211> LENGTH: 4
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 16

Ile Glu Pro Asp
1

<210> SEQ ID NO 17
<211> LENGTH: 4
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 17

Asp Glu Thr Asp
1

<210> SEQ ID NO 18
<211> LENGTH: 4
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 18

Trp Glu His Asp
1

<210> SEQ ID NO 19
<211> LENGTH: 4
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 19

Tyr Val Ala Asp
1

<210> SEQ ID NO 20
<211> LENGTH: 4
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 20

Asp Glu His Asp
1

<210> SEQ ID NO 21
<211> LENGTH: 4
<212> TYPE: PRT
<213> ORGANISM: Artificial sequence
```

-continued

```
<220> FEATURE:
<223> OTHER INFORMATION: Description of Artificial sequence: Protease
      recognition sequence

<400> SEQUENCE: 21

Asp Glu Val Asp
1

<210> SEQ ID NO 22
<211> LENGTH: 4
<212> TYPE: PRT
<213> ORGANISM: Artificial sequence
<220> FEATURE:
<223> OTHER INFORMATION: Description of Artificial sequence: Protease
      recognition sequence
<221> NAME/KEY: VARIANT
<222> LOCATION: (1)..(1)
<223> OTHER INFORMATION: Xaa is Trp or Ley

<400> SEQUENCE: 22

Xaa Glu His Asp
1

<210> SEQ ID NO 23
<211> LENGTH: 4
<212> TYPE: PRT
<213> ORGANISM: Artificial sequence
<220> FEATURE:
<223> OTHER INFORMATION: Description of Artificial sequence: Protease
      recognition sequence
<221> NAME/KEY: VARIANT
<222> LOCATION: (3)..(3)
<223> OTHER INFORMATION: Xaa is Ile or His

<400> SEQUENCE: 23

Val Glu Xaa Asp
1

<210> SEQ ID NO 24
<211> LENGTH: 4
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 24

Leu Glu Thr Asp
1

<210> SEQ ID NO 25
<211> LENGTH: 4
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 25

Leu Glu His Asp
1

<210> SEQ ID NO 26
<211> LENGTH: 4
<212> TYPE: PRT
<213> ORGANISM: Artificial sequence
<220> FEATURE:
<223> OTHER INFORMATION: Description of Artificial sequence: Protease
      recognition sequence
```

```
<221> NAME/KEY: VARIANT
<222> LOCATION: (1)..(3)
<223> OTHER INFORMATION: Xaa is any amino acid

<400> SEQUENCE: 26

Xaa Xaa Xaa Asp
1

<210> SEQ ID NO 27
<211> LENGTH: 8
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 27

Arg Pro Leu Gly Ile Ile Gly Gly
1               5

<210> SEQ ID NO 28
<211> LENGTH: 3
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 28

Glu Gly Arg
1

<210> SEQ ID NO 29
<211> LENGTH: 3
<212> TYPE: PRT
<213> ORGANISM: Artificial sequence
<220> FEATURE:
<223> OTHER INFORMATION: Description of Artificial sequence: Protease
      recognition sequence

<400> SEQUENCE: 29

Val Leu Lys
1
```

PROTEASE SPECIFIC CLEAVABLE LUCIFERASES AND METHODS OF USE THEREOF

FIELD OF THE INVENTION

The present invention relates generally to polynucleotides encoding luciferase polypeptides and more specifically to the use of luciferase and variants thereof to detect protease activity, agents that modulate protease activity, and methods of identifying agents that modulate apoptosis.

BACKGROUND

Proteases play essential roles in many disease processes such as Alzheimer's, hypertension, inflammation, apoptosis, and AIDS. Compounds that block or enhance their activity have potential as therapeutic agents. Because the normal substrates of peptidases are linear peptides and because established procedures exist for making non-peptidic analogs, compounds that effect the activity of proteases are natural subjects of combinatorial chemistry. Accordingly, screening compounds produced by combinatorial chemistry requires a convenient enzymatic assays.

Apoptosis is a physiological mechanism of cell death which involves the fragmentation of a cell into membrane-bound particles. The process of apoptosis is involved in a variety of normal and pathogenic biological events, both during development and in adulthood. Agents which affect apoptosis may have therapeutic utility in treating diseases and disorders characterized by aberrant cell proliferation or death (reviewed in Hoeppner et al., Biochim. Biophys. Acta 242: 217–220, 1966; Thompson, Science 267:1456–1462, 1995). Techniques for detection of apoptosis may be useful to screen for potential therapeutic agents that may induce or prevent apoptosis.

Caspases are a class of proteins central to the apoptotic program and are cysteine protease having specificity for aspartate as a substrate cleavage site. These proteases are primarily responsible for the degradation of cellular proteins that lead to the morphological changes seen in cells undergoing apoptosis. For example, one of the caspases identified in humans was previously known as the interleukin-1$\beta$ (IL-1$\beta$) converting enzyme (ICE), a cysteine protease responsible for the processing of pro-IL-1$\beta$ to the active cytokine. Overexpression of ICE in Rat-1 fibroblasts induces apoptosis (Miura et al., Cell 75:653, 1993).

The Caspase family proteases have been found to play an essential role in the intracellular pathway of apoptosis (reviewed in Martin et al., Cell 82:349–352 1995). ICE itself is not a mediator of apoptosis in most mammalian cell types. Rather, a family of homologous proteases comprising at least nine human ICE family proteases have been identified to date (ICE, CPP32/apopain/Yama, ICH-1, TX/ICH-2/ICE$_{rel}$ III, ICE$_{rel}$ III, MI-L1/MH-3/ICE-LAP3, Mch2, FLICE/Mch5, ICE-LAP6/Mch6), each of which leads to apoptosis when over-expressed in a proteolytically active form in cultured mammalian cells (Miura et al., Cell 75:653–660 1993; Wang et al., Cell 78:739–750 1994; Fernandes-Alnemri et al., J. Biol. Chem. 269:30761–30764 1994; Faucheu et al., EMBO J. 14:1914–22, 1995; Kamens et al., J. Biol. Chem, 270:15250–15256, 1995; Alnenui et al., J. Biol. Chem. 270:4312–4317, 1995; Fernandes-Alnemri et al., Cancer Res. 55:6045–6052, 1995; Lippke et al., J. Biol. Chem. 271:1825–1828, 1996; Muzio et al., Cell 85:817–827, 1996; Duan et al., J. Biol. Chem. 271:16720–16724, 1996). Moreover, treatment of cells with apoptotic stimuli increases ICE-like proteolytic activity in cell extracts (Los et al., Nature 375:81–83, 1995; Enari et al., Nature 380:723–726, 1996).

Degradation of specific cellular proteins following the activation of an ICE-like protease, has also been associated with apoptosis. For example, poly(ADP-ribose)polymerase (PARP) is cleaved specifically during apoptosis in mammalian cells (Kaufmann et al., Cancer Res, 53:3976–3985, 1993) and is an excellent substrate in vitro for several ICE homologues (Tewari et al., Cell 81:801–809, 1995; Nicholson et al., Nature 375:37–43, 1995; Gu et al., J. Biol. Chem. 270:18715–18718, 1995; Fernandes-Alnemri et al., Cancer Res. 55:2737–2742, 1995, Fernandes-Alnemri et al., ibid.; Lippke et al., J. Biol. Chem. 271:1825–1828, 1996). Protease inhibitors which block the activity of ICE homologues prevent not only apoptosis, but PARP degradation as well (Schlegel et al., ibid.).

Due to the inadequacies in many of the known methods for the detection of cell apoptosis, there continues to be a need for new, selective methods of detection.

SUMMARY OF THE INVENTION

The present invention overcomes many of the problems in the art by providing an isolated polypeptide characterized as having luciferase activity and a recognition site specifically cleavable by a protease, wherein cleavage results in a decrease in luciferase activity. The polypeptides and polynucleotides encoding the polypeptides of the invention are useful in characterizing and identifying cellular processes associated with metabolism, cell growth and cell death (e.g., apoptosis). In addition, the methods and compositions of the invention are useful in identifying agents that modulate cellular activity and particularly protease activity (e.g., caspase activity associated with apoptosis).

In one embodiment, the invention provides a luciferase polypeptide that is specifically cleavable by a protease. In one embodiment, the luciferase activity is *Renilla* luciferase activity. In another embodiment, the recognition site is a peptide sequence selected from the group consisting of DEVD, VEHD, LETD, LEHD, IEPD, DETD, WEHD, YVAD, VEID, and any combination thereof. In another embodiment, the polypeptide has a sequence as set forth in SEQ ID NO:4.

The invention also provides an isolated polynucleotide encoding a polypeptide characterized as having luciferase activity and a recognition site specifically cleavable by a protease. Cleavage of the expressed polypeptide results in a decrease in luciferase activity. In one embodiment, the polynucleotide has a sequence as set forth in SEQ ID NO:3.

In addition, the invention provides a vector containing a polynucleotide encoding a polypeptide characterized as having luciferase activity and a recognition site specifically cleavable by a protease, wherein cleavage results in a decrease in luciferase activity. In one embodiment, the vector is an expression vector. In another embodiment, the vector is a plasmid.

The invention further provides a host cell containing a vector of the invention. The host cell can be prokaryotic or eukaryotic.

The invention also provides a method of identifying a protease activity modulator (e.g., inhibitor or activator). The method includes contacting a sample containing a protease and a polypeptide characterized as having luciferase activity and a recognition site specifically cleavable by the protease, wherein cleavage results in a decrease in luciferase activity, with an agent suspected of modulating the protease activity and detecting luciferase activity in the sample before and after contacting with the agent. An increase in luciferase activity after contacting with the agent is indicative of an agent that inhibits the protease activity and a decrease in luciferase activity is indicative of an activator of protease activity.

The invention provides a method of identifying a caspase activity modulator (e.g., inhibitor or activator). The method includes contacting a sample containing a caspase-family protease with an agent suspected of modulating the caspase activity and a polypeptide characterized as having luciferase activity and a cleavage site cleavable by the caspase, wherein cleavage of the polypeptide modulates luciferase activity, and detecting luciferase activity in the sample before and after contacting with the agent. An increase in luciferase activity after contacting with the agent is indicative of an agent that inhibits caspase activity. A decrease in luciferase activity is indicative of an activator of caspase activity.

The invention further provides a method of identifying a modulator of apoptosis. The method includes contacting a sample containing a caspase-family protease with an agent suspected of modulating the caspase activity and a polypeptide characterized as having luciferase activity, wherein the polypeptide includes a cleavage site cleavable by the caspase, such that cleavage of the polypeptide modulates luciferase activity. Luciferase activity is detected in the sample before and after contacting with the agent. An increase in luciferase activity after contacting with the agent is indicative of an agent that inhibits apoptosis and a decrease in luciferase activity is indicative of an activator of apoptosis activity.

The invention further provides a kit useful for the detection of caspase activity. The kit includes a carrier means with at least two containers. The first container contains a polypeptide or a polynucleotide encoding the polypeptide characterized as having luciferase activity and a cleavage site cleavable by a caspase-family protease, wherein cleavage results in a decrease in luciferase activity, and the second container containing a luciferase substrate (e.g., coelenterazine).

The invention also provides a method of producing a polypeptide characterized as having luciferase activity and a recognition site specifically cleavable by a protease. The method includes culturing the host cell containing a vector of the invention under conditions to express the polypeptide; and recovering the expressed polypeptide.

Also provided is a fusion protein having a luciferase polypeptide domain and a polypeptide of interest linked to the N-terminal or C-terminal end of the luciferase domain.

DETAILED DESCRIPTION OF THE INVENTION

Figure 1:
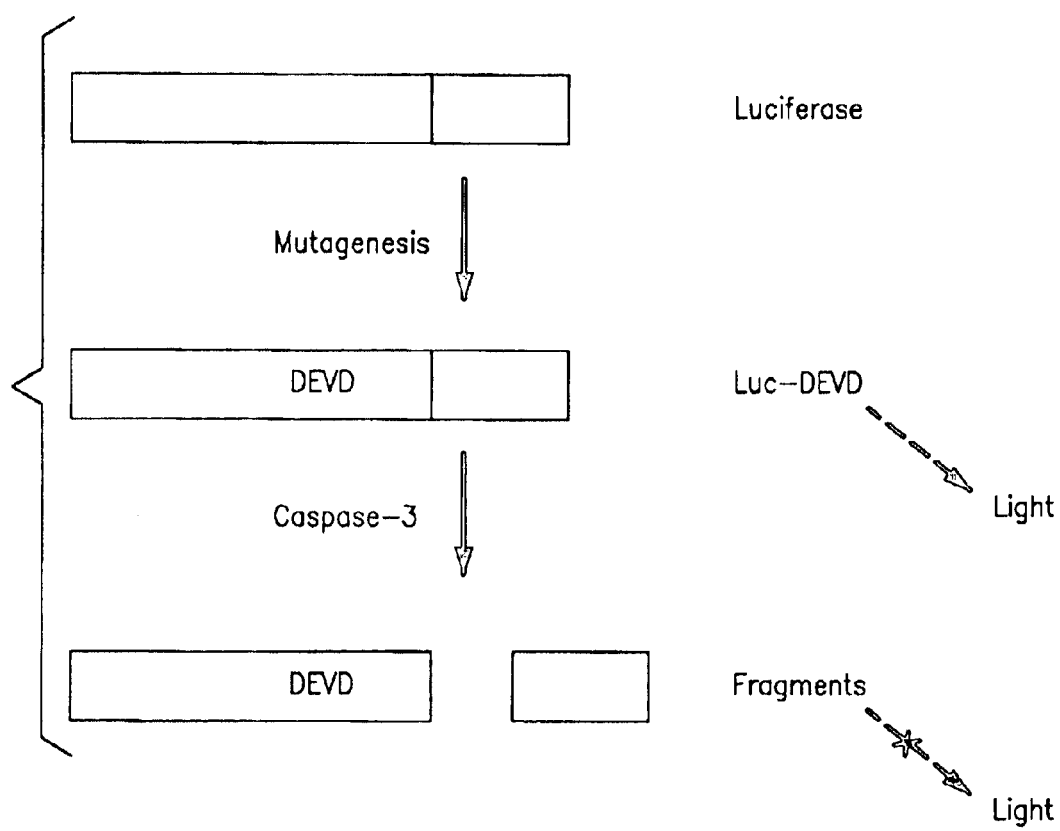
FIG. 1 is a schematic demonstrating the general process of the invention. In the schematic a luciferase is modified to include a cleavable peptide sequence (e.g. DEVD) which when cleaved by a protease (e.g., caspase-3) inhibits luciferase activity.

The *Renilla*, also known as sea pansies, belong to a class of coelenterates known as the anthozoans. In addition to *Renilla*, other representative bioluminescent genera of the class Anthozoa include Cavarnularia, Ptilosarcus, Stylatula, Acanthoptilum, and Parazoanthus. All of these organisms are bioluminescent and emit light as a result of the action of an enzyme (luciferase) on a substrate (luciferin) under appropriate biological conditions. Prior studies have demonstrated that all of the above-mentioned anthozoans contain similar luciferases and luciferins. See, for example, Cormier et al., J. Cell. Physiol. 81: 291–298, 1973. The luciferases and luciferins from each of these anthozoans will crossreact with one another to produce the characteristic blue luminescence observed in *Renilla* extracts. Each of these luciferases has similar biochemical properties, and the biochemical requirements for bioluminescence are identical regardless of the anthozoan from which the luciferase was derived.

There has been considerable interest of late in replacing radioactive labels used in analytical assays with other types, such as luminescent labels. Firefly luciferase, which is a molecule of significantly different structure that does not react with *Renilla*-like luciferins, is one molecule that has been proposed for use as such labels. However, firefly luciferase suffers from a number of deficiencies that make this molecule less than optimal in biological assays. For example, ATP acts as a trigger of the firefly luciferase system, and the ubiquitous nature of ATP makes control of this variable difficult.

The photoprotein aequorin (which consists of apoaequorin bound to a coelenterate luciferin molecule) and *Renilla* luciferase both utilize the same coelenterate luciferin, and the chemistry of light emission in both cases has been shown to be the same. However, aequorin luminescence is triggered by calcium, does not require dissolved oxygen, and represents a single turnover event. In contrast, *Renilla* luciferase requires dissolved oxygen in order to produce light in the presence of coelenterate luciferin. *Renilla* luciferase also acts as a true enzyme, catalyzing a long-lasting luminescence in the presence of saturating levels of luciferin.

Sub-attomole levels of aequorin can be detected with photometers even though its luminescence represents a single turnover event. *Renilla* luciferase, because of its enzymatic ability, should be detectable at levels 1 to 2 orders of magnitude lower than aequorin. Furthermore, *Renilla* luciferase is known to be relatively stable to heat, an important consideration for assays that often involve incubation at physiological temperatures. Accordingly, *Renilla* luciferase is a potentially useful label for biological and other assays.

Since the DNA sequence of the *Renilla* luciferase gene has been identified, it is possible to produce a DNA gene entirely by synthetic chemistry, after which the gene can be inserted into any of the many available DNA vectors using known techniques of recombinant DNA technology. Thus, the invention can be carried out using reagents, plasmids, and organisms which are freely available and in the public domain at the time of filing of this patent application without requiring a deposit of genetic material.

A luciferase is an enzyme that catalyzes a reaction to produce light. There are a number of different luciferase enzymes derived or modified from various sources, including for example, firefly luciferase and *Renilla* luciferase. "*Renilla* luciferase" means the luciferase enzyme isolated from a member of the genus *Renilla* or an equivalent molecule obtained from any other source or synthetically.

The invention provides effective methods and compositions for measuring protease activity in vitro or in vivo. Such methods are of critical importance in identifying and characterizing cellular biochemical pathways as well as identifying diagnostic and therapeutic agents for modulating diseases or disorder associated with biochemical pathways. The polynucleotides and the polypeptides encoded by the polynucleotides provide compositions useful for measuring protease activity. The polypeptides of the invention are easily detectable and are sensitive to the presence or absence of protease activity. Accordingly, the polypeptides offer a substrate for measuring such activity. For example, caspase family proteases have been found to play a role in the intracellular pathway of apoptosis (reviewed in Martin et al., Cell 82:349–352 1995). In addition, degradation of specific cellular proteins by protease activity following the activation of an ICE-like protease, has been associated with apoptosis. Accordingly, identifying and providing protease inhibitors or activators of ICE homologues provide a method of modulating apoptosis and PARP degradation as well provide useful therapeutics for treating diseases or disorder associated with apoptosis.

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document.

As used herein and in the appended claims, the singular forms "a," "and," and "the" include plural referents unless the context clearly dictates otherwise. Thus, for example, reference to "a sample" includes a plurality of samples and reference to "the agent" generally includes reference to one or more agents and equivalents thereof known to those skilled in the art, and so forth.

All publications mentioned herein are incorporated herein by reference in full for the purpose of describing and disclosing the databases, proteins, and methodologies, which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The headings and subheadings used herein are for the convenience of the reader and are not intended to limit the invention.

Polynucleotides

The invention provides polynucleotides encoding polypeptides having luciferase activity. The polynucleotides include recombinantly modified sequences as well as sequences encoding fusion polypeptides. In one embodiment, the polynucleotide of the invention encodes a luciferase containing a recognition sequence cleavable by a protease. The recognition sequence can be engineered to be contained between the N- and C-terminal ends of an expressed polypeptide. Such recognition sequence can be designed based on the degeneracy of the genetic code, and typically will be engineered within the coding sequence to modify as few nucleic acid bases in a codon(s) as possible. In one embodiment, the polynucleotide encodes a luciferase construct containing a recognition sequence selected from the group consisting of DEVD, VEHD, LETD, LEHD, IEPD, DETD, WEHD, YVAD, VEID. In another embodiment, the polynucleotide encodes a polypeptide having a sequence as set forth in SEQ ID NO:2, wherein residues 197–200 are replaced by a recognition sequence selected from the group consisting of DEVD, VEHD, LETD, LEHD, IEPD, DETD, WEHD, YVAD, VEID. In another embodiment, the polynucleotide has a sequence as set forth in SEQ ID NO:1 or 3.

In addition, the polynucleotides of the invention (e.g., a polynucleotide having a sequence as set forth in SEQ ID NO:3) can be operably linked to a sequence encoding a second polypeptide sequence of interest to form a fusion construct. Upon expression of the fusion construct the fusion polypeptide will contain one or more moieties corresponding to a polypeptide having luciferase activity and the polypeptide sequence(s) of interest.

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence. In addition, polynucleotides greater than 100 bases long can be readily synthesized, for example, on an Applied Biosystems Model 380A DNA Synthesizer.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

Nucleic acid sequences can be created which encode a fusion protein and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having ammo acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant a minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of the polynucleotide sequence. Both constitutive and inducible promoters, are included in the invention (see e.g., Bitter et al., Methods in Enzymology 153:516–544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a polynucleotide encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a polynucleotide sequence encoding a luciferase polypeptide (e.g., a *Renilla* luciferase) of fragment thereof. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a polynucleotide encoding a polypeptide of the invention such that the localization or signal peptide is located at the amino terminal end of a resulting polynucleotide/polypeptide (see for example, Liu et al., "Secretion of functional *Renilla reniformis* luciferase by mammalian cells," Gene 203(2):141–8, 1997). The construction of expression vectors and the expression of genes in transfected cells involves the use of molecular cloning techniques also well known in the art. (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., Molecular Cloning A Laboratory Manual, Cold Spring Harbor Laboratory, N.Y., 1989).

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp. 516–544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673–684, 1987; and The Molecular Biology of the Yeast *Saccharomyces*, Eds. Strathern et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

An alternative expression system which could be used to express a luciferase polypeptide of the invention is an insect system. In one such system, *Autographa californica* nuclear polyhedrosis virus (ACNPV) is used as a vector to express foreign or mutated polynucleotide sequences. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *S. frugiperda* cells in which the inserted gene is expressed, see Smith, et al., J. Viol. 46:584, 1983; Smith, U.S. Pat. No. 4,215,051.

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a DNA molecule encoding a luciferase polypeptide of the invention or a fragment thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a luciferase polypeptide (e.g., a *Renilla* luciferase) and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, a polynucleotide encoding a *Renilla* luciferase may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a luciferase polypeptide or fragment thereof in infected hosts (e.g., see Logan & Shenk, Proc. Natl. Acad. Sci. USA, 81:3655–3659, 1984). Alternatively, the vaccinia virus 7.5K promoter may be used. (e.g., see, Mackett, et al., Proc. Natl. Acad. Sci. USA, 79:7415–7419, 1982; Mackett, et al., J. Virol. 49:857–864, 1984; Panicali, et al., Proc. Natl. Acad. Sci. USA 72:4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a luciferase gene (e.g., a *Renilla* luciferase) in host cells (Cone & Mulligan, Proc. Natl. Acad. Sci. USA, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a luciferase polypeptide of the invention controlled by appropriate expression control elements (e.g., promoter, enhancer, sequences, transcription terminators, polyadenylation sites, etc.), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including, but not limited to, the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt-cells respectively. Also, anti-metabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol. 150:1, 1981); and hygro, which confers resistance to hygromycin (Santerre, et al., Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature. For instance, if a nucleic acid sequence is inferred from a protein sequence, a primer generated to synthesize nucleic acid sequence encoding the protein sequence is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences. For example, primers can be synthesized based upon the amino acid sequence of a luciferase such as those set forth in SEQ ID NO:1 or 2 and can be designed based upon the degeneracy of the genetic code.

Polypeptides

The invention provides luciferase polypeptides characterized as having luciferase activity and a recognition sequence cleavable by a protease. Cleavage of the recognition sequence by a protease inhibits luciferase activity. The polypeptide can be any luciferase, including, for example, a *Renilla* luciferase. A polypeptide of the invention has a sequence as set forth in SEQ ID NO:2 wherein the sequence contains one or more recognition sequences. Examples of recognition sequences can be found in Table 1 below. In one embodiment, the polypeptide of the invention has a sequence as set forth in SEQ ID NO:2 wherein the recognition sequence replaces residues 197–200. In another embodiment, the polypeptide has a sequence as set forth in SEQ ID NO:4. The cleavable luciferase constructs or wild-type luciferase of the invention may also be operably linked to a polypeptide of interest to form a fusion protein as described herein. In addition, a luciferase of the invention can include a peptide or polypeptide sequence that targets the luciferase to a particular organelle, subcellular compartment, tissue, or cell type. Such modifications are within the scope of the invention and are based upon the ability to link amino acid sequences to the N-terminal or C-terminal region of the luciferase polypeptide of the invention. In one embodiment, a targeting sequence is linked to a luciferase polypeptide by a cleavable linker.

In one embodiment, a subcellular targeting sequence can be linked to a luciferase of the invention via a protease cleavable linker. Cleavable linkers include the peptide sequences presented in Table 1, below. In addition, subcellular fractionation is known in the art and commonly performed through, for example, differential centrifugation techniques. In one method of the invention, the luciferase is targeted to a subcellular organelle by the targeting sequence. The subcellular luciferase can be cleaved from the targeting sequence by a protease capable of cleaving the linker sequence. In the absence of a protease capable of cleaving the linker sequence a targeted luciferase will remain associated with the subcellular compartment. In the presence of a protease capable of cleaving the linker the luciferase will be cleaved from the targeting sequence and freely diffuse into other subcellular compartments or into the extracellular milieu.

Accordingly, luciferase fusion proteins comprising a targeting sequence linked to a luciferase polypeptide via a cleavable linker can be used to analyze protease activity in mammalian and human cells under a variety of conditions using techniques including, for example, subcellular fractionation. By subcellular fractionation one can determine whether a cleavable luciferase fusion protein remained with a targeted subcellular organelle or is found in a fraction other than the fraction containing the organelle where it was originally targeted. If the luciferase activity is found in a fraction containing the targeted organelle, this is indicative that there was not a protease capable of cleaving the linker. However, if the luciferase activity is found in a different fraction, this is indicative that a protease cleaved the linker molecule.

Examples of targeting sequence include nuclear or mitochondrial targeting sequence, which are fused to the N- or C-terminal end of a luciferase via a cleavable linker peptide (see Table 1). The nucleus contains many proteins that help mediate its unique functions. These proteins are imported from the cytosol where they are made. They must pass through both the outer and inner nuclear membranes to reach the inside of the nucleus (the nuclear lumen). This transport process is selective: many proteins made in the cytosol are excluded from the nucleus. Many nuclear proteins interact with receptor proteins located on the pore margin that actively transport the proteins into the nucleus while enlarging the pore channel. Cell compartmentalization domains (i.e., targeting sequences) are well known and include, for example, a plasma membrane localization domain, a nuclear localization signal, a mitochondrial membrane localization signal, an endoplasmic reticulum localization signal, or the like (see, for example, Hancock et al., *EMBO J.* 10:4033–4039, 1991; Buss et al., *Mol. Cell. Biol.* 8:3960–3963, 1988; U.S. Pat. No. 5,776,689 each of which is incorporated herein by reference). Such a domain can be useful to target an agent to a particular compartment in the cell.

Adding a localization signal to a luciferase can be performed using common molecular biology techniques known to those of skill in the art.

A "polypeptide" or "protein" refers to a polymer in which the monomers are amino acid residues which are joined together through amide bonds. When the amino acids are alpha-amino acids, either the L-optical isomer or the D-optical isomer can be used, the L-isomers being typical. A luciferase polypeptide is intended to encompass any amino acid sequence and include modified sequences such as glycoproteins, which provides a polypeptide having luciferase activity. Accordingly, the polypeptides of the invention are intended to cover naturally occurring proteins, as well as those which are recombinantly or synthetically synthesized. In one embodiment, the luciferase is a *Renilla* luciferase. In addition, a luciferase polypeptide can occur in at least two different conformations wherein both conformations have the same or substantially the same amino acid sequence but have different three dimensional structures so long as the have a biological activity related to a luciferase, such as a *Renilla* luciferase. Polypeptide or protein fragments of a luciferase are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general, two amino acid sequences are substantially the same or substantially homologous if they are at least 70% identical.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted, e.g. by the local homology algorithm of Smith & Waterman, Adv. Appl. Math. 2:482 (1981), by the homology alignment algorithm of Needleman & Wunsch, J. Mol. Biol 48:443 (1970), by the search for similarity method of person & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

On example of a useful algorithm is BLAST and BLAST 2.0 algorithms, which are described in Altschul et al., Nuc. Acids Res. 25:3389–3402, 1977, and Altschul et al, J. Mol. Biol. 215:403–410, 1990, respectively. Software for performing BLAST analyses is publicly available through the National Center for Biotechnology Information (http://www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications (see for example, Liu et al., Gene 237(1):153–9, 1999, which described modification to *Renilla* luciferase to increase stability). Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on. Whether a change results in a functioning peptide can readily be determined by direct analysis for function in an assay that relies on ability of the modified enzyme (or fragment) to carry out the normal function of the natural luciferase enzyme (or fragment). For example, modified peptides can be tested for their ability to catalyze the emission of light from coelenterate luciferin by the same techniques described below for the recombinant *Renilla* luciferase molecule. Alternatively, the modified sequences can be screened for functional activity by attaching a suitable substrate, e.g., a coelenterate luciferin molecule, to an affinity column and capturing modified peptides that are retained by the bound substrate.

Solid-phase chemical peptide synthesis methods can also be used to synthesize the polypeptide or fragments of the invention. Such method have been known in the art since the early 1960's (Merrifield, R. B., *J. Am. Chem. Soc.*, 85, 2149–2154 (1963) (See also Stewart, J. M. and Young, J. D., Solid Phase Peptide Synthesis, 2 ed., Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA*, 81, 3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

Functional fragments of a luciferase, based on these sequences and fragments and full length sequences representing minor variations thereof, will have at least some of the biological activities of luciferase and will therefore be useful in appropriate circumstances. For example, functional fragments of the luciferase enzyme sequence can be prepared and screened for use as luciferin binding site models. Peptide synthesizers (as described above) can be used to prepare peptide fragments (e.g., less than 100 amino acids) or techniques of genetic engineering can be used to prepare the peptide fragments. The fragments can then be screened for functional activity by attaching a suitable substrate, e.g., a coelenterate luciferin molecule, to an affinity column and capturing peptide fragments that are retained by the bound substrate.

Methods for Screening Protease Modulating Agents

The invention also provides methods of screening agents for agents capable of modulating protease activity. The methods of the invention are based, in part, on the protease sensitive luciferase of the invention. For example, in one embodiment, a method of identifying an agent capable of modulating apoptosis is provided. As discussed above, proteases, for example, caspase family proteases, have been associated with apoptosis. Thus, the method includes contacting a sample containing a caspase-family protease with an agent suspected of modulating the caspase activity and a caspase sensitive luciferase polypeptide having a cleavage site cleavable by the caspase, wherein cleavage of the polypeptide inhibits luciferase activity. The luciferase activity is detected in the sample before and after contacting with the test agent wherein an increase in luciferase activity after contacting with the agent is indicative of an agent that inhibits apoptosis and a decrease is indicative that the agent activates apoptosis.

Accordingly, the invention provides a screening system useful for identifying agents which modulate the cleavage of recognition sequence present in a luciferase polypeptide of the invention and detecting luciferase activity. This allows one to rapidly screen for protease activity modulators. Utilization of the screening system described herein provides a sensitive and rapid means to identify agents which modulate (e.g., inhibit or activate) a protease, for example, a caspase family protease.

"Modulation" refers to the capacity to either enhance or inhibit a functional property of biological activity or process (e.g., enzyme activity); such enhancement or inhibition may be contingent on the occurrence of a specific event, such as activation of a signal transduction pathway, and/or may be manifest only in particular cell types.

The term "modulator" refers to an agent (naturally occurring or non-naturally occurring), such as, for example, a biological macromolecule (e.g. nucleic acid, protein, non-peptide, or organic molecule), small molecules, or an extract made from biological materials such as bacteria, plants, fungi, or animal (particularly mammalian) cells or tissues. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in the screening assays described herein. The activities (or activity) of a modulator may be known, unknown or partial known. Such modulators can be screened using the methods of the invention.

The term "test agent" refers to an agent to be tested by one or more screening method(s) of the invention as a putative modulator. Usually, various predetermined concentrations are used for screening such as 0.01 uM, 0.1 uM, 1.0 uM, and 10.0 uM. Controls can include the measurement of a signal in the absence of the test agent, comparison to an agent known to modulate the target, or comparison to a sample (e.g., a cell, tissue or organism) before, during and/or after contacting with the test agent.

A luciferase polypeptide of the invention is useful as a substrate to study agents or conditions that cleave the recognition site (e.g., a cleavable peptide). In particular, the invention contemplates luciferase polypeptides in which the recognition site is a peptide moiety containing an amino acid sequence that is a cleavage site for a protease of interest. Accordingly, the invention provides methods to determine the amount of a protease in a sample by contacting the sample with a luciferase polypeptide of the invention and measuring changes in luciferase activity (see for example FIG. 2). The luciferase polypeptide can be produced by expression of a nucleic acid that encodes a luciferase polypeptide having a recognition site internal to the N- and C-terminal ends of the polypeptide, wherein the recognition site is cleavable by a protease. The luciferase polypeptide of the invention can be used for, among other things, monitoring the activity of a protease inside a cell that expresses the recombinant luciferase.

The recognition site, in the luciferase polypeptide of the invention, is typically a peptide moiety having a cleavage recognition site specific for an enzyme or other cleavage agent of interest. The cleavage site is useful because when a luciferase construct containing the cleavage site is mixed with the cleavage agent, the peptide is a substrate for cleavage by the cleavage agent. Cleavage of the moiety results in inhibition of the luciferase activity of the luciferase polypeptide.

When the cleavage agent of interest is a protease, the recognition site can comprise a peptide containing a cleavage recognition sequence for the protease. A cleavage recognition sequence for a protease is a specific amino acid sequence recognized by the protease during proteolytic cleavage. In particular, the cleavable moiety can contain any of the amino acid sequences in TABLE I. The sites are recognized by the enzymes as indicated and the site of cleavage is marked by a hyphen. Other protease cleavage sites also are known in the art and can be included in the cleavage moiety.

TABLE I

| Protease | Sequence |
| --- | --- |
| HIV-1 protease | SQNY-PIVQ (SEQ ID NO:5) |
|  | KARVL-AEAMS (SEQ ID NO:6) |
| Prohormone convertase | PSPREGKR-SY (SEQ ID NO:7) |
| Interleukin-1b-converting enzyme | YVAD-G (SEQ ID NO:8) |
| Adenovirus endopeptidase | MFGG-AKKR (SEQ ID NO:9) |
| Cytomegalovirus assemblin | GVVNA-SSRLA (SEQ ID NO:10) |
| Leishmanolysin | LIAY-LKKAT (SEQ ID NO:11) |
| β-Secretase for amyloid precursor protein | VKM-DAEF (SEQ ID NO:12) |
| Thrombin | FLAEGGGVR-GPRVVERH (SEQ ID NO:13) |
| Renin and angiotensin-converting enzyme | DRVYIHPF-HL-VIH (SEQ ID NO:14) |
| Cathepsin D | KPALF-FRL (SEQ ID NO:15) |
| granzyme B | IEP-D (SEQ ID NO:16) |
| C. elegans CED-3 | DET-D (SEQ ID NO:17) |
| caspase 1 | WEH-D, YVA-D (SEQ ID NO:18,19) |
| caspase 2 | DEH-D (SEQ ID NO:20) |
| caspase 3 | DEV-D (SEQ ID NO:21) |
| caspase 4 | (W/L)EH-D (SEQ ID NO:22) |
| caspase 5 | (W/L)EH-D (SEQ ID NO:22) |
| caspase 6 | VE(I/H)-D (SEQ ID NO:23) |
| caspase 7 | DEV-D (SEQ ID NO:21) |
| caspase 8 | LET-D (SEQ ID NO:24) |
| caspase 9 | LEH-D (SEQ ID NO:25) |
| matrix metalloproteinase | RPLGIIGG (SEQ ID NO:27) |
| urokinase-type plasminogen activator (uPA) | EGR (SEQ ID NO:28) |
| plasmin | VLK (SEQ ID NO:29) |

See, e.g., Matayoshi et al. (1990) Science 247:954, Dunn et al. (1994) Meth. Enzymol. 241:254, Seidah & Chretien (1994) Meth. Enzymol. 244:175, Thornberry (1994) Meth. Enzymol. 244:615, Weber & Tihanyi (1994) Meth. Enzymol. 244:595, Smith et al. (1994) Meth. Enzymol. 244:412, Bouvier et al. (1995) Meth. Enzymol. 248:614, Hardy et al. (1994) in Amyloid Protein Precursor in Development, Aging, and Alzheimer's Disease, ed. C. L. Masters et al. pp. 190–198, Thornberry et al. (1997) J. Biol. Chem. 222(29): 17907.

Caspase cleavage sites are of particular interest due to their relationship to apoptosis (Thornberry et al. J. Biol. Chem. 22(29):17907–17911, 1997; Tang et al. J. Biol. Chem. 274(1):7245–7252, 1999). Caspases cleave their substrates after an Aspartate in a recognition sequence of four amino acids with the conserved Aspartate. The recognition sequence has the general consensus of XXXD (SEQ ID NO:26).

In the case of a known protease with cleavage activity of unknown or partially defined specificity, a library of randomized recognition sequences can be used in place of a predetermined recognition sequence in the luciferase polypeptide in order to determine the sequences cleaved by a protease. The method can be used with a recombinant protease constructed with a novel cleavage specificity. This method can also be used to determine the specificity of cleavage of an orphan protein that reveals sequence homology to a known protease structure or group of proteases.

As used herein, a "library" refers to a collection containing at least 5 different members, preferably at least 100 different members and more preferably at least 200 different members. Each member of a luciferase library comprises a luciferase polypeptide sequence containing a recognition sequence, typically a peptide sequence of variable amino acid composition, wherein cleavage of the recognition sequence results in reduction of luciferase activity. The amino acid sequences for the recognition sequence may be completely random or biased towards a particular sequence based on the homology between other proteases and the protease being tested. The location of the recognition sequence will typically correspond to amino acid sequences present in the native luciferase having about 25% to 90% homology with the recognition sequence. For example, a DEVD (SEQ ID NO:21) recognition sequence at positions 197–200 of SEQ ID NO:2 has 25% homology to the native Renilla luciferase sequence (SEQ ID NO:2). The library can be chemically synthesized, which is particularly desirable if D-amino acids are to be included. In most instances, however, the library will be expressed in bacteria or a mammalian cell.

The luciferase polypeptides of the invention can be synthesized as discussed above or encoded by polynucleotide sequences that can be expressed in vivo or in vitro. Recombinant luciferase polypeptides can be produced by expression of nucleic acid encoding the luciferase construct in any number of host cells (as described above).

The polypeptide can also contain a tag to simplify isolation of the luciferase polypeptide. For example, a polyhistidine tag of, e.g., six histidine residues, can be incorporated at the amino terminal end of the luciferase polypeptide. The polyhistidine tag allows convenient isolation of the polypeptide in a single step by nickel-chelate chromatography.

In another embodiment, a vector containing a polynucleotide encoding a luciferase polypeptide of the invention may be incorporated into a cell or an entire organism by standard recombinant DNA techniques or, where the organism is a multicellular organism, through transgenic or gene replacement techniques. An expression vector capable of expressing the enzyme optionally may be incorporated into the entire organism by standard transgenic or gene replacement techniques. Then, a sample containing a cell or a sample from the organism containing the luciferase construct is tested. For example, cell or tissue homogenates, individual cells, or samples of body fluids, such as blood, can be tested.

The assays of the invention can be used to screen drugs to identify compounds that alter the activity of a protease that cleaves the luciferase construct. In one embodiment, the assay is performed on a sample in vitro containing a protease. A sample containing a known amount of protease is mixed with a cleavable luciferase polypeptide of the invention and with a test agent. The amount of the protease activity in the sample is then determined as above, e.g., by determining the degree of luciferase activity at a first and second time after contact between the sample, the luciferase construct and the agent. Then the amount of activity per mole of protease in the presence of the test agent is compared with the activity per mole of protease in the absence of the test agent. A difference indicates that the test agent alters the activity of the protease. Accordingly, the alterations may be an increase in protease activity resulting in a decrease in luciferase activity or a decrease in protease activity corresponding to an increase or maintenance of luciferase activity.

In one embodiment, the ability of an agent to alter protease activity is determined. In this assay, cells are conditioned or contacted with an agent suspected of modulating protease activity. The cell or cells in the culture are lysed and protease activity measured. For example, a lysed cell sample containing a known or unknown amount of protease is mixed with a cleavable luciferase polypeptide of the invention. The amount of the protease activity in the sample is then determined as above, e.g., by determining the degree of luciferase activity in a control or non-treated sample and the treated lysed cellular sample. The activity or inhibition can be calculated based on a per microgram or milligram protein in the sample. Accordingly, the modulation of protease activity includes an increase in protease activity resulting in a decrease in luciferase activity or a decrease in protease activity corresponding to an increase or maintenance of luciferase activity. Typically, the difference is calibrated against standard measurements to yield an absolute amount of protease activity. A test agent that inhibits or blocks the activity or expression of the protease can be detected by increased luciferase activity in treated cells compared to untreated controls.

In another embodiment, the ability of an agent to alter protease activity in vivo is determined. In an in vivo assay, cells transfected with an expression vector encoding a luciferase polypeptide of the invention are exposed to different amounts of the test agent, and the effect on luciferase activity in a cell can be determined. Typically, the difference is calibrated against standard measurements to yield an absolute amount of protease activity. A test agent that inhibits or blocks the activity or expression of the protease can be detected by increased luciferase activity in treated cells compared to untreated controls.

Kits

The materials and composition for use in the assay of the invention are ideally suited for the preparation of a kit. Such a kit may comprise a carrier means containing one or more container means such as vials, tubes, and the like, each of the container means comprising one of the separate elements to be used in the method. One of the container means comprises a luciferase polypeptide or polynucleotide (e.g., in the form of a vector) of the invention. A second container may contain a luciferase substrate (e.g., coelenterazine).

The following examples are offered by way of illustration and are not to be construed as limiting the invention.

EXAMPLE 1

Site-Directed Mutagenesis by PCR and Cloning of Mutated *Renilla* Luciferase Gene into pGEX4T1

From SeaLite's plasmid pCR3.1 (SeaLite Sciences, Inc., Norcross, Ga.), *Renilla* Luciferase polynucleotide corresponding to the N-terminal sequence (Amino acid 1-204) of *Renilla* Luciferase was amplified by PCR with oligo primers containing the N-terminal sequence ATG site and a DEVD mutation sequence at amino acid residues 197–200. The C-terminal sequence (amino acid 193 to stop codon) was amplified by PCR with oligo primers containing a DEVD mutations sequence at amino acid residues 197–200 and a C-terminal sequence stop codon. The intact mutated *Renilla* luciferase polynucleotide sequence was amplified by PCR using the mixture of the above N and C-terminal gene fragments as template and oligo primers containing N-terminal sequences from ATG site and C-terminal sequence from stop codon. The mutated polynucleotide sequence was cloned into bacterial expression vector pGEX4T1 (Amersham Pharmacia Biotechnology) at EcoRI and XhoI sites. The cloned polynucleotide was sequenced from both DNA strands to verify that the sequence was as expected. The cloned luciferase sequence matched the reported GenBank sequence completely except for the mutated DEVD site. The recombinant plasmid pGEX4T1-RLuc-EEFA was transform into *E. Coli* BL31 (DE3)pLyeE (Invitrogen) for expression of GST-RLuc-EEFA recombinant protein.

Expression and Purification of GST-RLuc-EEFA

A single colony of transformants was selected and inoculated into 5 ml of LB$^{amp}$ culture and grown overnight. The 5 ml culture was then inoculated into 500 ml of LB$^{amp}$ and grow at 37° C. with vigorous shaking, until OD$_{600}$ was 0.5–0.7.

Expression of the cloned luciferase was induce by adding IPTG, 1 mM final, to the bacterial culture and incubating the culture for an additional 4 h. The cells were harvested by centrifugation for 5 min at 10000×g and resuspended in 20 ml of 1× PBS. The cells were lysed by sonication and the cell lysate collected after centrifugation for 10 min at 15000×g. Two ml of 50% GS-Agarose bead slurry were added to the cell lysate and incubated for 1 h with gentle shaking. The beads were washed 3 times with PBS and the bound GST fusion protein eluted with 10 mM Glutathione in 50 mM Tris, pH 8.0. The eluted protein was dialyzed against PBS overnight at 4° C. Protein concentration was determined by BCA assay (Pierce).

Caspase-3 Activity Assay

Figure 2:
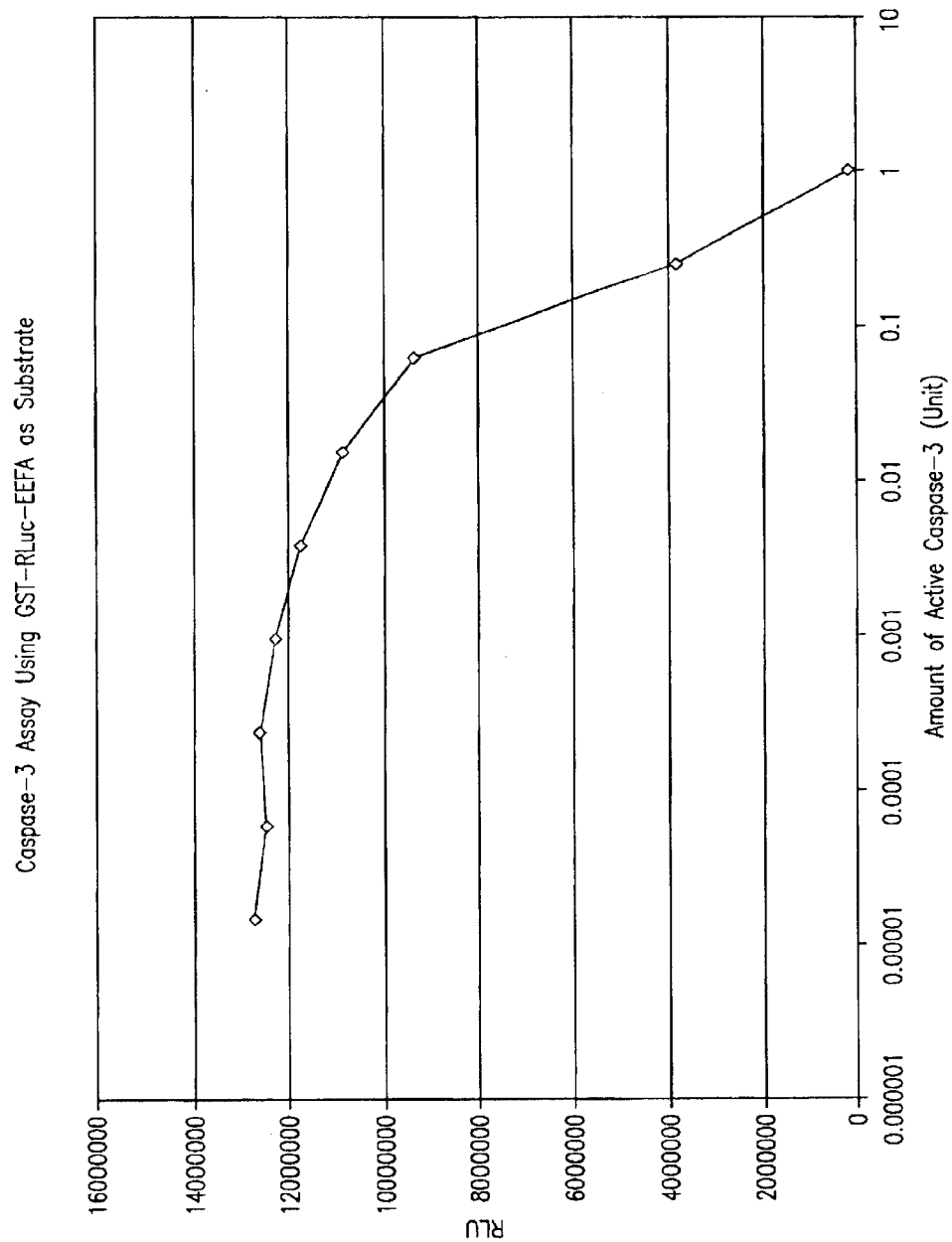
FIG. 2 shows a plot of luciferase activity in the presence of various amounts of caspase-3.
Figure 5:
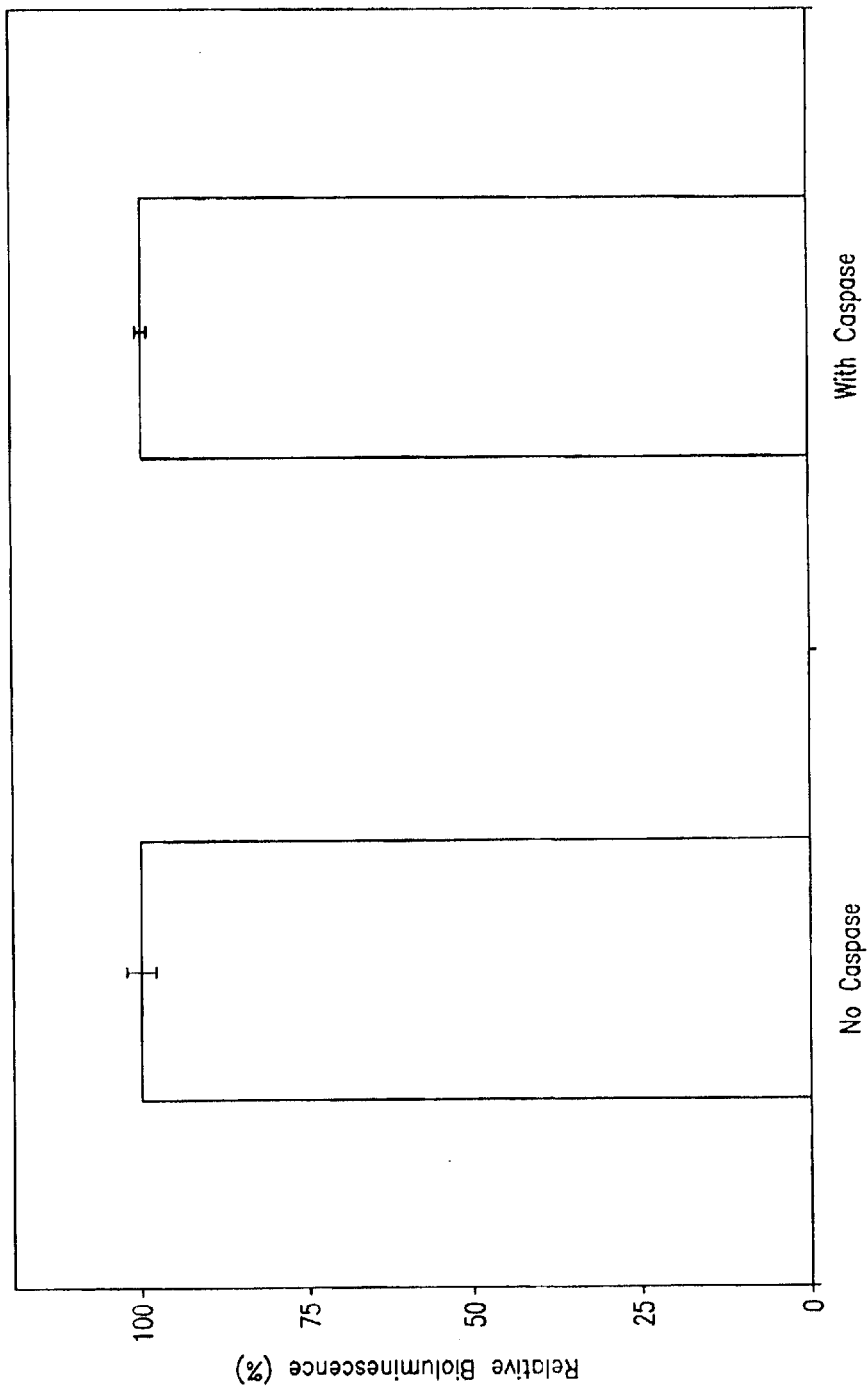
FIG. 5 shows the effect of caspase-3 on a GST-luciferase fusion polypeptide.
Figure 6:
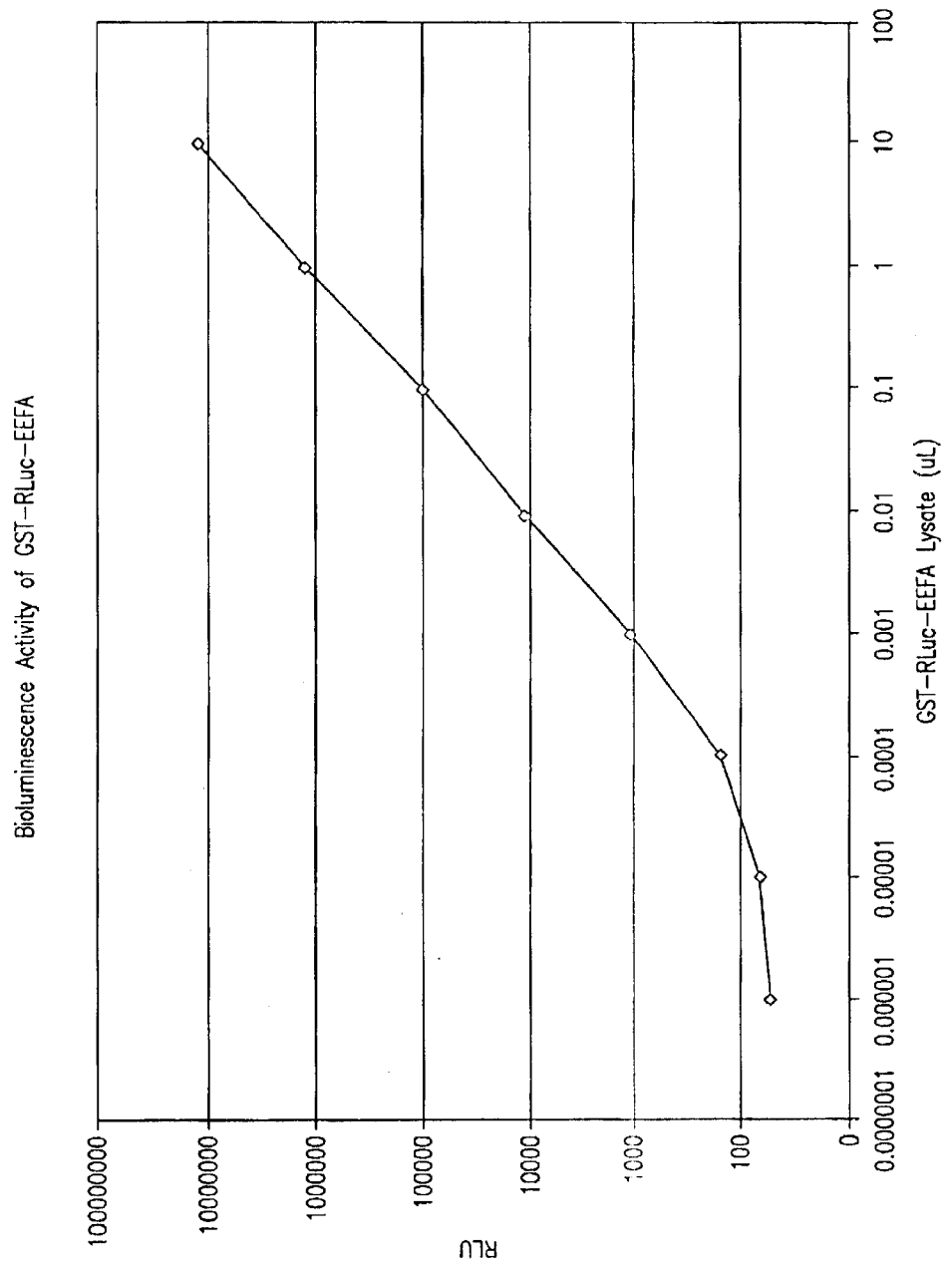
FIG. 6 shows a plot of luciferase activity at various concentrations of a fusion polypeptide of the invention.

For bioluminescence assay, 5 μl of purified luciferase protein or cell lysate containing GST-RLuc or GST-RLuc-EEFA was used to replace the colorimetric substrate APC-DEVD-pNA of the Caspase-3 and Caspase-3 Colorimetric Assay Kit (Chemicon) in a final volume of 30 μl. After a 2 h incubation at 37° C., 10 μl of the mixture was transferred into 96-well plate, 200 μl of luciferase substrate coelenterazine (1 μM) was injected. Light production was measure for a 15-second period immediately upon the addition of the substrate (FIGS. 2 and 5).

Figure 3:
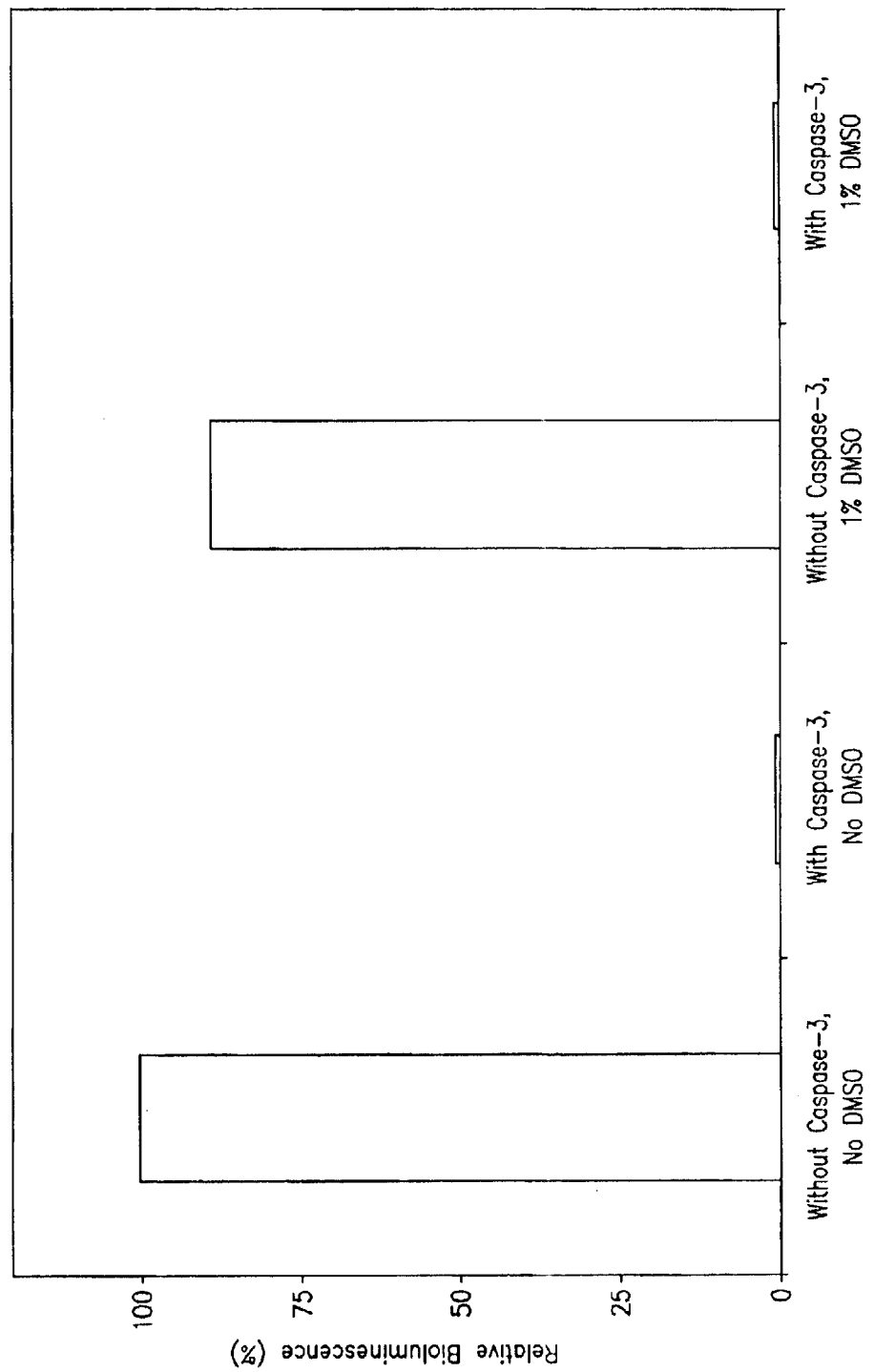
FIG. 3 shows a bar graph measuring the effect of DMSO on caspase-3 activity in the presence of a cleavable polypeptide of the invention.

DMSO Effect: DMSO was added to the caspase assay mixture at 1% DMSO final and the assay carried out as described above (FIG. 3).

Figure 4:
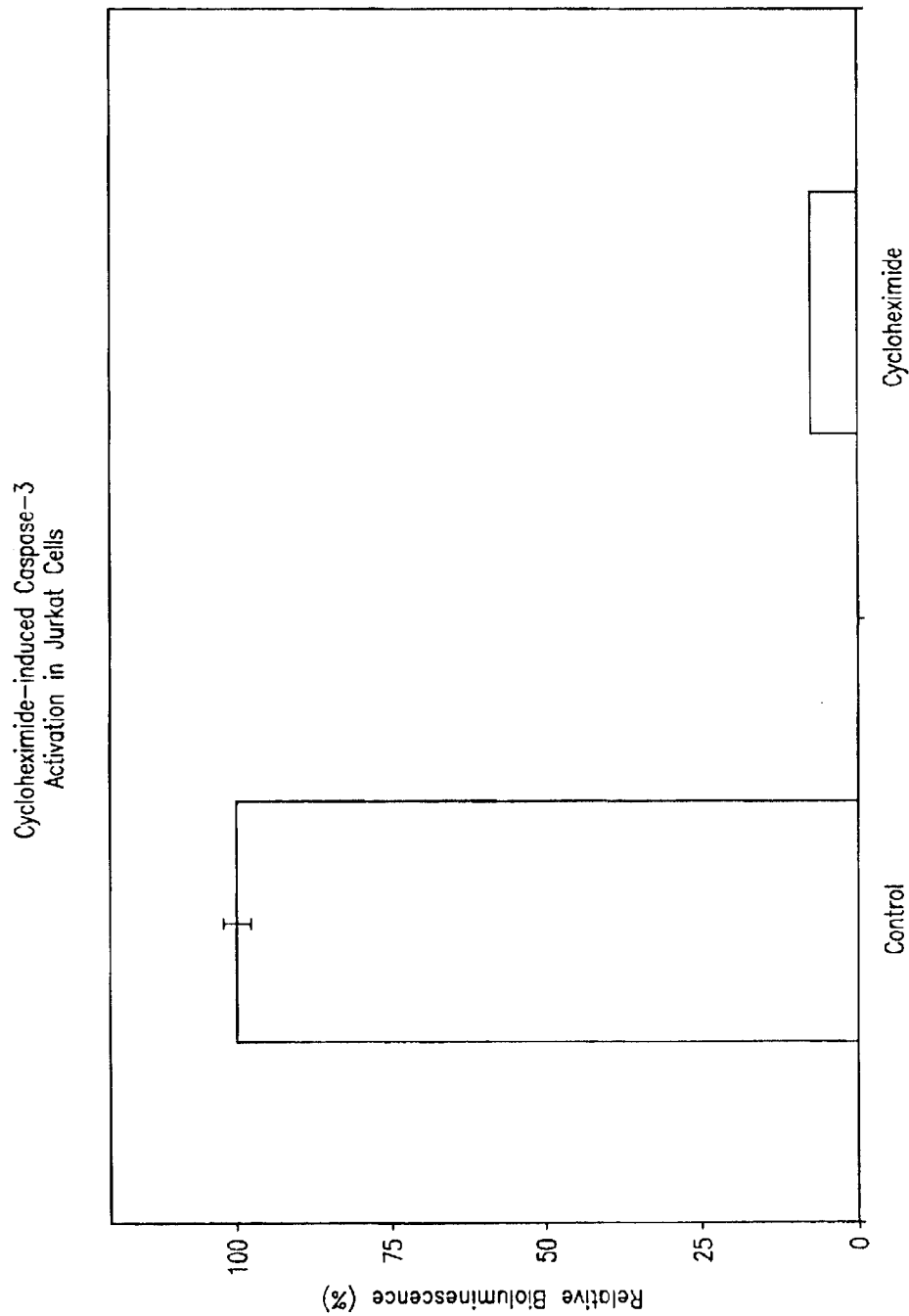
FIG. 4 shows a bar graph demonstrating the effect cycloheximide-induced caspase-3 activation in Jurkat cells using a caspase-3 clevable luciferase.

Cell Lysates from Jurkat T cells: Cells were treated with 20 μg/ml cycloheximide (20 mg/ml stock in DMSO) for 6 h and then lysed. The cells were pelleted by centrifugation and the cell pellet lysed in passive lysis buffer. Caspase assay: 10 μl of Jurkat lysate (DMSO alone or cycloheximide), 5 μl of GST-RLuc-EEFA, and 15 μl of 2× caspase assay buffer were combined and incubated for 2 hour at 37° C. Ten μl of the mixture was then transferred for bioluminescence activity (FIG. 4).

While the invention has been described in detail with reference to certain preferred embodiments thereof, it will be understood that modifications and variations are within the spirit and scope of that which is described and claimed.

What is claimed is:

1. A purified polypeptide characterized as having *Renilla* luciferase activity and a recognition site specifically cleavable by a protease, wherein cleavage results in a decrease in luciferase activity and wherein the recognition site is at residues 197–200 of SEQ ID NO:2, wherein the recognition site is a peptide sequence selected from the group consisting of DEVD (SEQ ID NO: 21), VEHD (SEQ ID NO: 23, wherein X is H), LETD (SEQ ID NO: 24) LEHD (SEQ ID NO: 22, wherein X is L or SEQ ID NO: 25) IEPD (SEQ ID NO: 16), DETD (SEQ ID NO: 17), WEHD (SEQ ID NO: 22, wherein X is W or SEQ ID NO: 18), YVAD (SEQ ID NO: 19), VEID (SEQ ID NO: 23, wherein X is I), and any combination thereof.

2. The purified polypeptide of claim 1, wherein the polypeptide has a sequence as set forth in SEQ ID NO:4.

3. The purified polypeptide of claim 1, wherein the protease is a caspase-family protease.

4. The purified polypeptide of claim 3, wherein the caspase-family protease is selected from the group consisting of a Caspase-3, a Caspase-6, a Caspase-8, and a Caspase-9.

5. The purified polypeptide of claim 3, wherein the caspase is a Caspase-3.

* * * * *